(12) United States Patent
White et al.

(10) Patent No.: US 6,688,466 B2
(45) Date of Patent: Feb. 10, 2004

(54) PACKAGING FOR PERSONAL CARE PRODUCTS

(75) Inventors: Lisa White, Neenah, WI (US); Donald G. Fox, The Villages, FL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 40 days.

(21) Appl. No.: 09/998,375

(22) Filed: Nov. 30, 2001

(65) Prior Publication Data
US 2003/0102238 A1 Jun. 5, 2003

(51) Int. Cl.⁷ .............................................. B65D 73/00
(52) U.S. Cl. .................... 206/440; 206/457; 206/459.5; 206/459.1
(58) Field of Search .............................. 206/45.2, 45.21, 206/45.24, 45.25, 45.28, 45.29, 457, 459.1, 459.5, 767, 494, 440; 229/87.18, 87.19, 922, 923; 40/312, 313

(56) References Cited
U.S. PATENT DOCUMENTS

| | | | | |
|---|---|---|---|---|
| 1,628,121 A | * | 5/1927 | Covel | 229/116.5 |
| 3,918,631 A | * | 11/1975 | Hackenberg | 229/208 |
| 4,955,469 A | * | 9/1990 | Hudspith | 206/45.23 |
| 5,044,547 A | * | 9/1991 | Hartman | 229/175 |
| 6,173,837 B1 | * | 1/2001 | Marconi | 206/457 |
| 6,454,095 B1 | * | 9/2002 | Brisebois et al. | 206/494 |

* cited by examiner

Primary Examiner—David T. Fidei
(74) Attorney, Agent, or Firm—Dority & Manning

(57) ABSTRACT

A packaging system for any manner of personal care products includes a package member configured for receipt of the personal care products therein. The external surface of the package member has a nondescript configuration that is generally not indicative of the types of products carried in the package. A flap member is connected to and repositionable on the external surface of the package member. A first side of the flap member may have product identifying indicia thereon, and a second opposite side of the flap member has a nondescript surface configuration that is not indicative of the personal care products within the package. Attaching devices are disposed to removeably secure the flap member in a first position on the external surface of the package such that the first side having the product identifying indicia thereon is outwardly facing, and in a second position wherein the flap member is flipped over and the second side having the nondescript configuration is outwardly facing.

23 Claims, 4 Drawing Sheets

PACKAGING FOR PERSONAL CARE PRODUCTS

BACKGROUND OF THE INVENTION

The present invention relates to packaging of personal care products, and in particular to a packaging system that offers a greater degree of privacy and discreteness to consumers.

"Personal care products" are generally known in the art as products of a personal hygiene or health care nature. Such products include, for example, incontinence articles, diapers, feminine hygiene products, etc. These products are typically packaged so that there is no question to the consumer as to what the package contains. Additionally, certain product information must be displayed on the package and be clearly visible to consumers. Unfortunately, conventional packaging also announces to everyone else at the point of purchase exactly what articles the individual is purchasing. As a result, the purchasing of such products can be an embarrassing, anxious, and often traumatic experience for certain individuals.

The storage of personal care products, particularly feminine hygiene products, can also be problematic. Most individuals value their personal privacy and prefer not to advertise to others in their living quarters that personal care products are present or necessary. However, in relatively tight or cramped living quarters (i.e., small apartments, college dorms, recreational vehicles, campers, etc.) cabinet or closet storage space is often unavailable in which to "hide" personal care products and it is often necessary that such products are stored in plain view. This situation can be embarrassing and distressing.

A need thus exists in the art for a discreet packaging system that disguises or "hides" the fact that personal care products are contained within the package yet does not detract from the purchasing individual's ability to accurately discern and identify the product at the point of sale or purchase.

SUMMARY

Objects and advantages of the invention will be set forth in part in the following description, or may be obvious from the description, or may be learned through practice of the invention.

The present invention relates to a unique packaging system for personal care products. The packaging system may be used for packaging any type of personal care product, for example incontinence articles or pads, and has particular usefulness for packaging feminine hygiene products, including sanitary pads, liners, tampons, etc. All such uses are within the scope and spirit of the invention.

The packaging system for personal care products according to the invention includes a package member that is configured for receipt of personal care products therein. The package member may be any conventional type of package or container, including a box, carton, soft-side package, etc. The package member includes an external surface having a desired nondescript aesthetic configuration or appearance. In other words, one viewing the package from the outside is not given any noticeable indication that the package contains personal care products. The aesthetic configuration of the package may include any manner of print, color, etc.

The packaging system includes a flap member connected to and variably positionable on the external surface of the package member. The flap member has a first side that may have product identifying indicia thereon. Alternatively, the product identifying indicia, or additional indicia, may be provided on the package member. The opposite or second side of the flap member has a nondescript aesthetic surface configuration or appearance that generally does not give an indication of the personal care products contained within the package. For example, the second side of the flap member may include the same type of nondescript surface configuration as the package member. In an alternative embodiment, the second side may include a completely different nondescript surface configuration as compared to that of the package member. The flap member may have an end that is permanently fixed to the external surface of the package member such that the flap member can be alternately folded to expose either the first or second sides. In an alternate embodiment, the flap member may be completely removable and simply be flipped over to expose the alternate sides.

Any type of conventional attaching device or devices, such as adhesives, hook-and-loop fasteners, etc., are employed to removably secure the flap member in a first position on the external surface of the package member such that the first side of the flap member having the product identifying indicia thereon is outwardly facing. In an embodiment wherein product indentifying indicia is provided directly on the package, the flap member is at a location on the package in its first position so as not to cover the indicia on the package. This would be the typical position of the flap member when the products are, for example, displayed on store shelves, etc., wherein it is necessary for the product identifying indicia to be readily visible to a consumer. However, once the consumer has decided to purchase the product, the consumer can easily flip, fold, or otherwise reposition the flap member so that the first side is adjacent to the external surface of the package member and covers any identifying indicia on the package, and the second side of the flap member having the nondescript configuration is outwardly facing and visible.

It may be desirable that nondescript purchasing indicia, such as a pricing barcode or the like, be placed on the package member at a location such that it is not covered up upon repositioning the flap member to the second position. In this manner, it is not necessary at the checkout counter or other point of purchase to reposition the flap member to the first position in order to identify the product for pricing.

For embodiments wherein the package member is a carton or box shaped member, there is at least one wall that is perpendicular to oppositely facing parallel walls of the package member. In this embodiment, an attached end of the flap member may be hinged to this perpendicular wall such that in the first position, the flap member lies against a first wall of the package member and, in the second position, the flap member lies against the opposite parallel wall. In embodiments wherein the package is more rounded or cylindrical, the flap member may be flexible or pliant so as to conform to the shape of the package in either the first or second position. The flap member may be hinged to the package member by any conventional means. In a particularly simple embodiment, the flap member is formed from a bendable or pliable material, such as a film, plastic, paper, etc., and is simply attached to the package member at one end thereof so that it can be easily bent or folded along the attachment line in a living-hinge configuration.

For various reasons after the package has been purchased, it may be desired that the flap member be capable of being removed from the package member. In this embodiment, the flap member may be scored or perforated at the end thereof attached to the package member so that a consumer can ultimately remove the flap member.

The present invention also encompasses packages of personal care products that incorporate the packaging system as discussed above and described in further detail herein.

The packaging system according to the invention will be described in greater detail below through use of the appended figures.

DETAILED DESCRIPTION

Reference will now be made in detail to one or more embodiments of the invention as illustrated in the Figures. Each embodiment is provided by way of explanation of the invention, and not meant as a limitation of the invention. For example, features illustrated or described as part of one embodiment may be used with another embodiment to yield still a further embodiment. It is intended that the present invention cover these and other modifications and variations as come within the scope and spirit of the invention.

Figure 1:
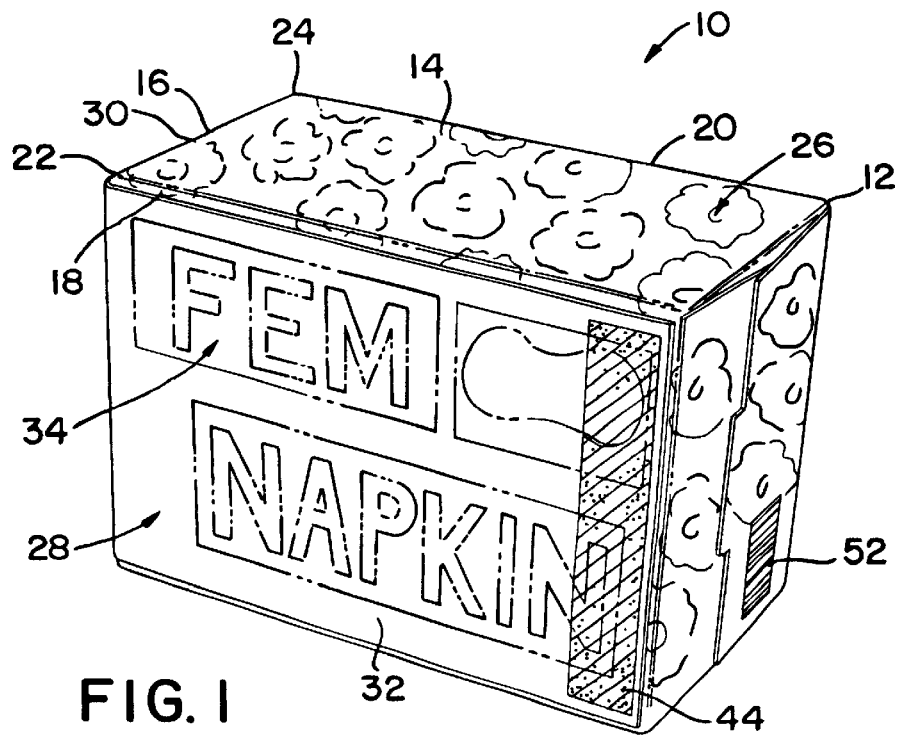
FIG. 1 is a perspective view of an embodiment of the packaging system for personal care products according to the invention.
Figure 2:
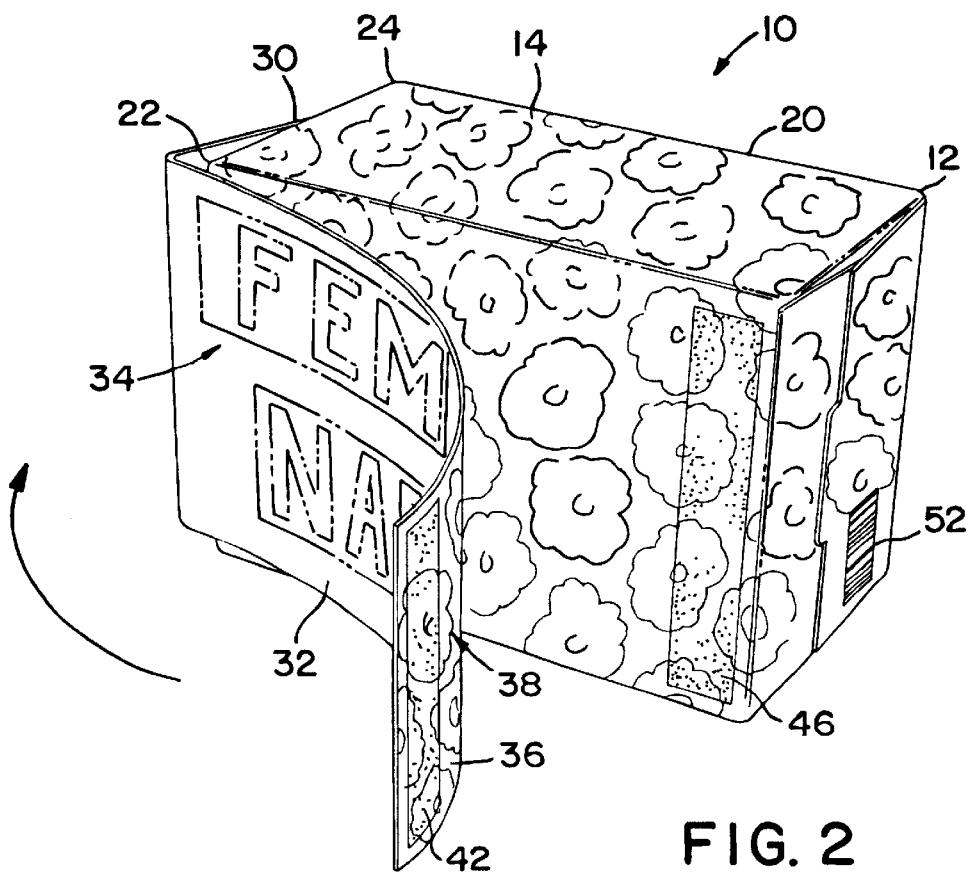
FIG. 2 is a perspective view of the package of FIG. 1 particularly showing the repositionable flap member.
Figure 5:
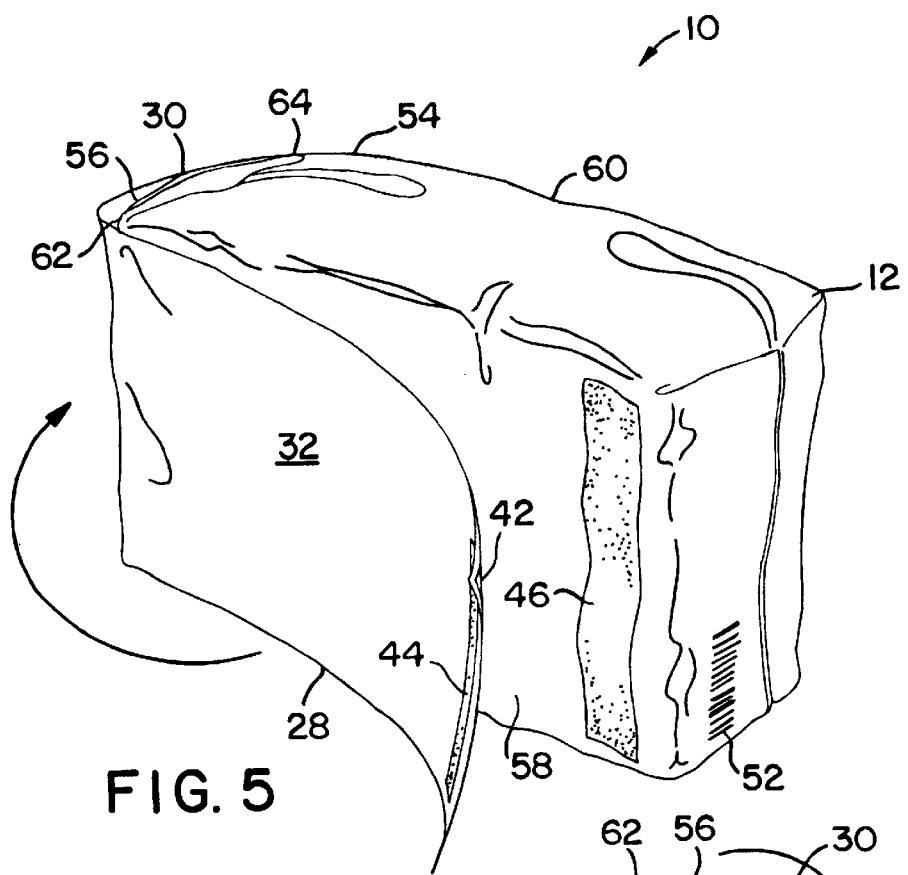
FIG. 5 is an alternative embodiment of a soft-side packaging system according to the invention and particularly illustrates the repositionable flap member.
Figure 6:
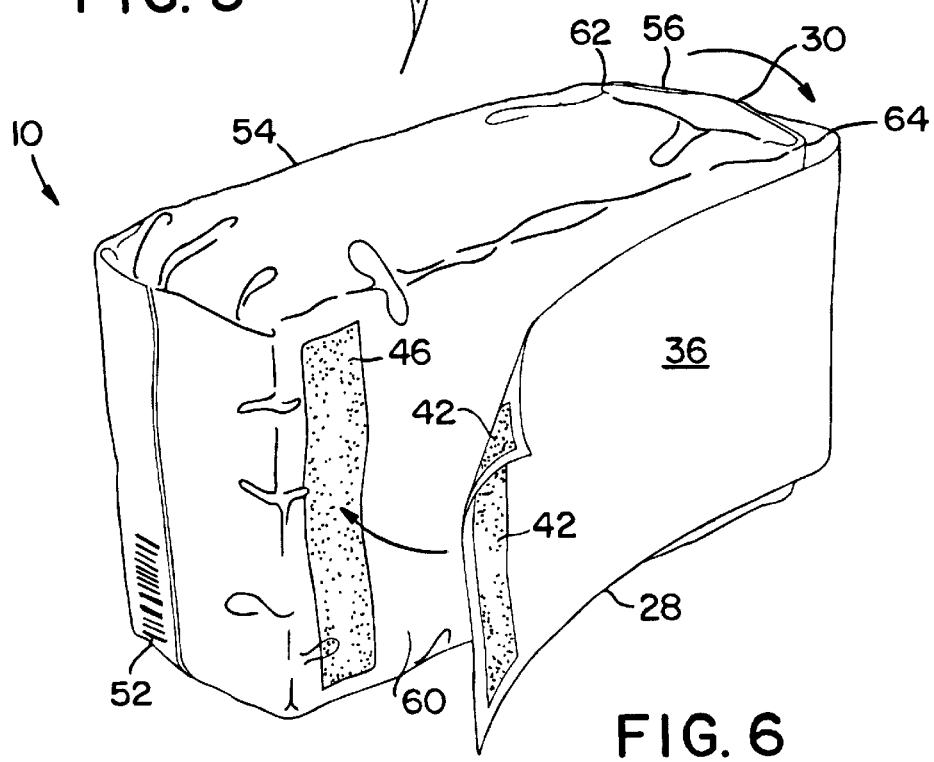
FIG. 6 is a perspective view of the package of FIG. 5 showing the second position of the flap member.
Figure 7:
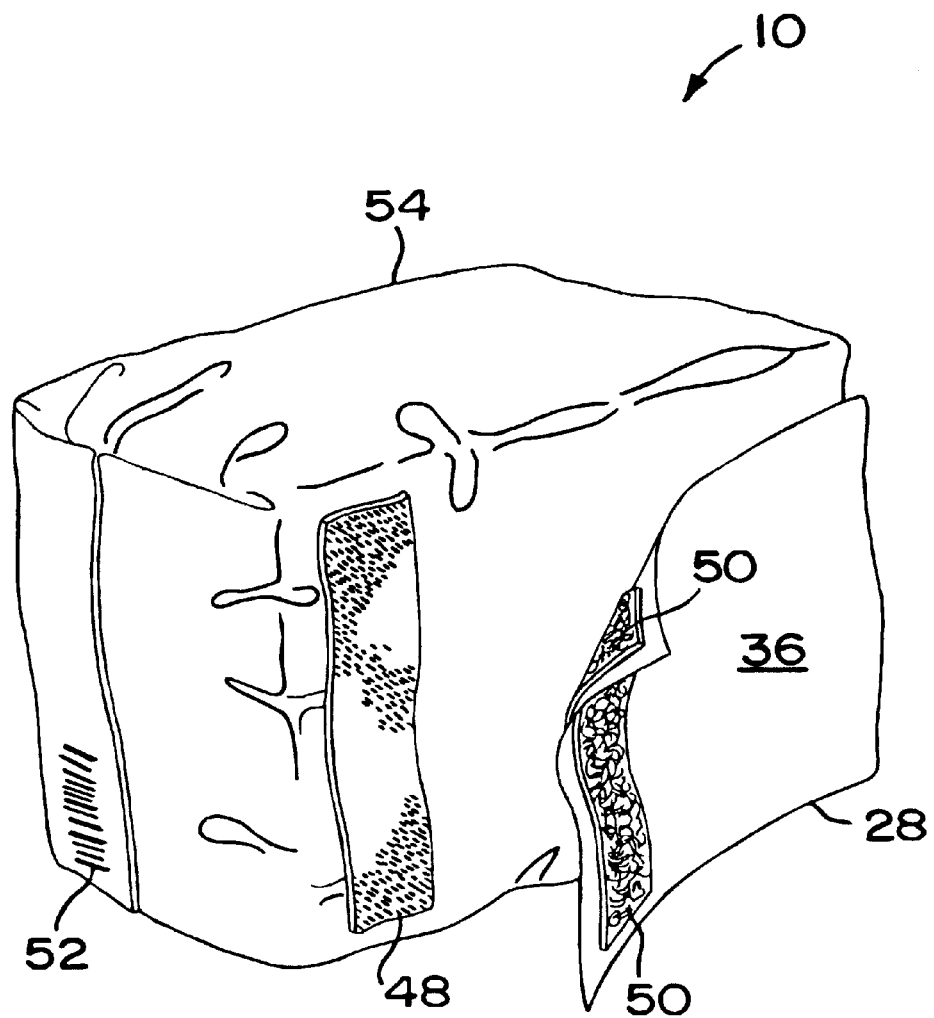
FIG. 7 is a partial perspective view of the package of FIG. 5 particularly illustrating an alternative attaching device for the flap member.

FIG. 1 illustrates a packaging system, generally 10, for personal care products according to the invention. It should be appreciated that the packaging system 10 is not limited in use to any particular type of personal care product. The packaging system 10 is illustrated as a packaging system for feminine care products, such as pads, liners, tampons, etc. in that this is a particularly useful application of the invention. However, the packaging system is just as useful for other types of personal care products, including incontinence articles, diapers, etc. The packaging system 10 includes a package member 12 configured for receipt of personal care products therein. The package member 12 may take on any manner of conventional package, such as the box or carton illustrated in FIGS. 1–4. In an alternative embodiment, the package member 12 may be a soft-side package 54 as illustrated in FIGS. 5–7. These types of packages are well known and used in the industry and a detailed description thereof is not necessary for purposes of understanding the present invention.

The package member 12 includes an external surface having a visible nondescript aesthetic configuration, generally 26, over at least a substantial portion thereof. This visual surface configuration 26 is "nondescript" in that it does not advertise or otherwise give an indication of the personal care products contained within the package member 12. For example, in the embodiment illustrated in FIGS. 1–4, the nondescript surface configuration is a floral pattern. It should be appreciated that any combination of patterns, colors, etc. may be utilized in this regard to provide a generally pleasing and nondescript surface configuration for the package member 12. The package member 12 may contain product identifying indicia thereon at a location that will be covered upon repositioning of a flap member, as described below.

The packaging system 10 includes a flap member 28 that is connected to but variably positionable on the package member 12. This may be accomplished in various ways. In the embodiment illustrated in FIGS. 1–4, the flap member 28 has an end 30 connected to a wall 16. The wall 16 is a common perpendicular wall to oppositely facing walls 18 and 20. The end 30 is connected to the perpendicular wall 16 generally in the middle thereof. It should be appreciated, however, that the flap member 28 may be connected at any position along any of the walls of the box member 12. In the soft-side bag 54 configuration of FIGS. 5–7, the flap member 28 has its end 30 attached to the common perpendicular wall 56 generally in the middle of the wall. Again, it should be appreciated that the flap 28 can be connected anywhere along the surface of the soft-side bag 54. It should also be appreciated that the flap member 28 may be completely removable from the box member 12 or bag 54 so as to be simply flipped over and reattached to the same side or a different side of the box or bag.

The flap member 28 has a first side 32 that may have any manner of product identifying indicia printed thereon. This indicia may be the sole indicia or in addition to any indicia on the package member 12. The totality of the indicia adequately describes and identifies the personal care products contained within the package member 12. Referring to FIGS. 1 and 5, the flap member 28 is positionable on the package member 12 in a first position such that the first side 32 is outwardly facing and any product identifying indicia 34 is readily visible to a potential consumer. The flap member 28 is held against a surface of the package member 12 by appropriate attaching devices, as described in greater detail below. In the embodiment illustrated in FIG. 1, the flap member 28 is held against the wall 18 of the box member 12 perpendicular to the end wall 16 where the end 30 of the flap member is attached. Referring to FIG. 5, the flap member 28 is similarly positioned so that the first surface 32 having product identifying indicia thereon is disposed against the wall 58 perpendicular to the end wall 56 where the end 30 of the flap member is attached.

The flap member 28 has an opposite or second side having a nondescript aesthetic surface configuration thereon. As with the nondescript surface configuration of the box member 12, the nondescript surface configuration of the second side 36 may be any pattern, color, etc. that provides a generally pleasing aesthetic visual appearance without giving any noticeable indication of the personal care products carried within the package member 12.

Figure 3:
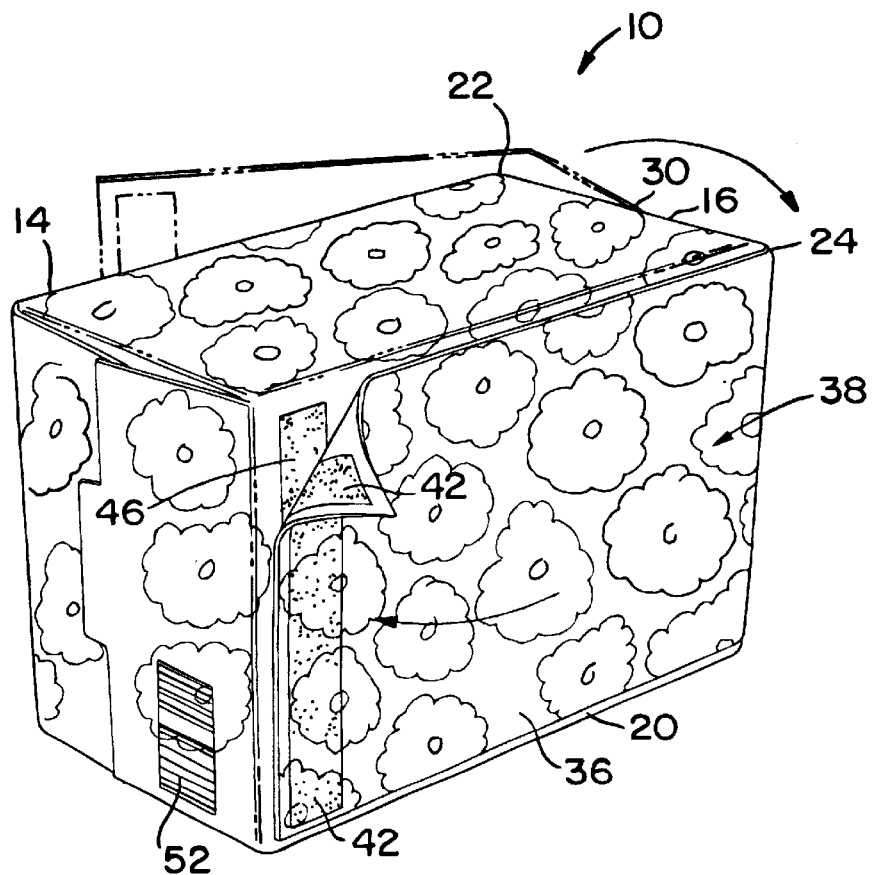
FIG. 3 is a perspective view of the package of FIG. 1 particularly illustrating the flap member in its second position.

The flap member 28 is positionable from the position shown in FIG. 1 to the position shown in FIG. 3 such that any product identifying indicia 34 on the first surface 32 is hidden from view and the nondescript surface configuration 38 of the second side 36 is outwardly facing and thus visible. Also, in the second position of the flap member 28, any product identifying indicia on the package member 12 is covered by the flap member. In a relatively simple embodiment, the flap member 28 is hinged at its end 30 so that it can simply be flipped over or folded around the box member 12, as illustrated in FIGS. 2, 3, 5, and 6. This feature may be accomplished in any number of ways. For example, the flap member 28 may be a flexible or pliant material, such as a film, paper, or the like, that is adhered at its end 30 to the surface of the box member 12. In this manner, the pliant flap member 28 can simply be folded along the adhesion line in a living-hinge type of arrangement. The flap member 28 is pliant so that it can conform to the shape of the box as it is repositioned from its first position illustrated in FIGS. 1 and 5 to its second position illustrated in FIGS. 3 and 6. For example, referring to FIGS. 1–3, the flap member 28 is attached in the middle of the common perpendicular wall 16, wraps around the corner 22, and is held against the external surface of wall 18. To reposition the flap member 28, a consumer detaches the flap member 28 from the first wall 18, and flips the flap member 28 around the box member 12, as indicated by the arrow in FIG. 2, such that the flap member 22 wraps around the corner 24 and is held against the external surface of wall 20, as illustrated in FIG. 3. The soft-side embodiment of FIGS. 5–7 operates in similar fashion. In its first position, the flap member 28 wraps around corner 62 and is attached to the wall 58 so that the surface 32 with the product identifying indicia (not shown) is outwardly facing. In its second position, the flap member 28 wraps around the corner 64 and is attached to the wall 60 so that the non-descript surface configuration of the flap surface 36 is outwardly facing.

Any manner of suitable attaching devices are provided on either or both of the flap member 22 and external surfaces of the package member 12 in order to releaseably secure the flap member 28 in its alternate positions. In the embodiment illustrated in FIGS. 1–3, a releasable adhesive 42 may be provided on each side of the flap member 28 generally in any pattern and at any location sufficient for securing the flap member to the package member. In the illustrated embodiment, the adhesive is applied in a strip at the end of the flap member. Referring to FIG. 1, a release liner 44 may be attached to the adhesive on the first side 32. To reposition the flap member 22, a consumer would peel the release liner 44 from the adhesive in order to reposition the flap member 44 to the position illustrated in FIG. 3. Once repositioned, the consumer may, if desired, place the release liner 44 on the exposed adhesive 42 on the second side 36 of the flap member, or simply dispose of the release liner. The adhesive 42 may be of the type such that it can be readily manually peeled or removed from the second side 36. In order to ensure that the flap member 28 is easily peeled or removed from the wall 18 so as to be repositioned onto the wall 20, a release material 46 may be provided on the wall 18 and/or wall 20. This release material 46 may be desired if the material of the package member 12 is not compatible with a releasable adhesive. The release material 46 would prevent damage to the flap member 28 or package member 12 in this regard.

Figure 4:
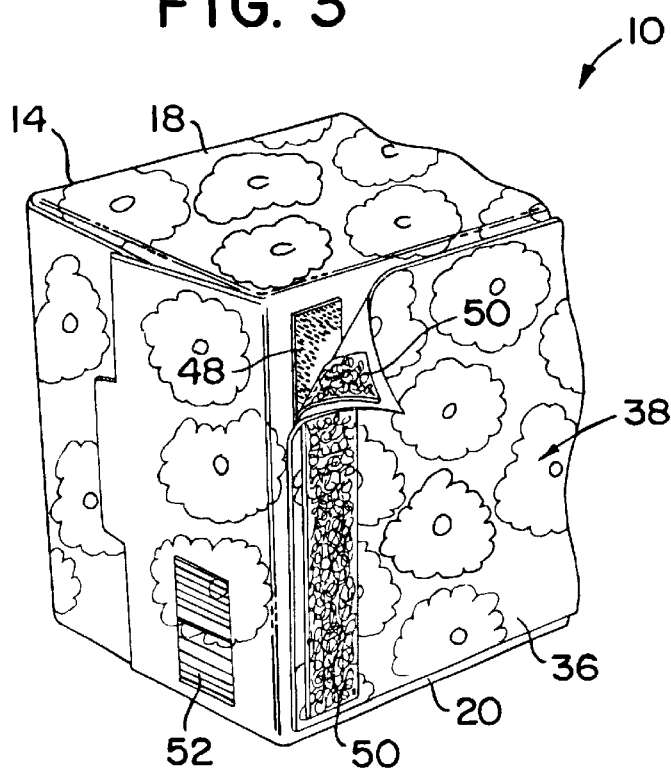
FIG. 4 is a partial perspective view of the package of FIG. 1 particularly illustrating an alternate attaching device for the flap member.

FIGS. 4 and 7 illustrate an alternative embodiment of a suitable attaching device. In this embodiment, a conventional hook-and-loop type fastening system is used. For example, a strip of hook material 48 may be provided on each of the walls 18 and 20 at an appropriate location. A complimentary loop material 50 may be provided on each side of the flap member 28 for releasable attachment with the hook material 48. In an alternative embodiment, the hook material 48 may be provided on the flap member 28 and the loop material 50 may be provided on the package member 12.

It may be desired to provide product pricing or other identifying indicia, such as a barcode 52, at a location on the package member 12 that is not covered by the flap member 28 in either of its positions. In this manner, the package can be accurately scanned or priced at the checkout counter or point of purchase without having to reposition the flap member 28 back to its first position.

Though not particularly illustrated in the Figures, it should also be appreciated that the flap member 28 may be removeably hinged or attached to the package member 12 so that after purchase of the products, a consumer may completely remove the flap member 28 from the package if so desired. The flap member 28 may be removeably attached to the package member by any conventional means, including a releasable adhesive, score line, perforation line, etc.

It should be appreciated by those skilled in the art that various modification or variations can be made to the embodiments of the packaging system illustrated and described herein without departing from the scope and spirit of the invention. It is intended that the invention include such modifications and variations as come within the scope of the appended claims and their equivalents.

What is claimed is:

1. A packaging system for personal care products, said system comprising:

a package member configured for receipt of personal care products therein, said package member comprising an external surface having a desired nondescript aesthetic configuration that is generally not indicative of the personal care products within said package member;

a flap member connected to and variably positionable on said external surface of said package member, said flap member having a first side and a second opposite side having a surface with nondescript aesthetic indicia or designs that is generally not indicative of the personal care products within said package member;

attaching devices disposed to removably secure said flap member in a first position on said external surface of said package member such that said first side is outwardly facing, and in a second position wherein said flap member is repositioned so that said second side is outwardly facing on said package member;and wherein said first side of said flap member has product identifying indicia thereon.

2. The packaging system as in claim 1, wherein said package member is a generally rigid sided box-like structure.

3. The packaging system as in claim 1, wherein said package member is a generally soft-side bag-like structure.

4. The packaging system as in claim 1, wherein said package member comprises at least one wall that is perpendicular to oppositely facing parallel walls, an end of said flap member hingedly attached to said perpendicular wall wherein in said first position, said flap member lies against a first wall of said package member, and in said second position said flap member lies against said oppositely facing parallel wall.

5. A packaging system for personal care products, said system comprising:

a package member configured for receipt of personal care products therein, said package member comprising an external surface having a desired nondescript aesthetic configuration that is generally not indicative of the personal care products within said package member;

a flap member connected to and variably positionable on said external surface of said package member, said flap member having a first side and a second opposite side having a surface with nondescript aesthetic indicia or designs that is generally not indicative of the personal care products within said package member;

attaching devices disposed to removably secure said flap member in a first position on said external surface of said package member such that said first side is outwardly facing, and in a second position wherein said flap member is repositioned so that said second side is outwardly facing on said package member; and wherein said aesthetic surface configuration of said flap member second side generally conforms to that of said package member.

6. The packaging system as in claim 1, wherein said attaching devices comprise hook-and-loop devices.

7. The packaging system as in claim 6 wherein said flap member comprises one of said hook material and said loop material on each of said first and second sides, and said respective other of said hook material and said loop material is disposed on said external surface of said package member at locations for proper orientation of said flap member in said first and second positions.

8. The packaging system as in claim 1, wherein said attaching devices comprise a releasable adhesive.

9. The packaging system as in claim 8, wherein said adhesive is applied to each of said first and second sides of said flap member.

10. The packaging system as in claim 1, wherein an end of said flap member is hingedly attached to said external surface of said package member.

11. The packaging system as in claim 10 comprising a living hinge configured between said flap member and said external surface of said package member.

12. The packaging system as in claim 1, further comprising necessary purchasing indicia provided on said external surface of said package member at a location such that said purchasing indicia is visible when said flap member is in said second position.

13. The packaging system as in claim 1, wherein said flap member is completely removable from said package member.

14. The packaging system as in claim 13, wherein said flap member is scored at an end thereof attached to said package member.

15. A package of personal care products, said package comprising:

an outer package member having said personal are products carried therein, said package member comprising an external surface having a desired nondescript aesthetic configuration that is generally not indicative of the personal care products within said package member;

a flap member having an end connected to said external surface of said package member, said flap member having a first side with product identifying indicia thereon, and a second opposite side having a surface with nondescript aesthetic indicia or designs that is generally not indicative of the personal care products within said package member; and attaching devices disposed to removably secure said flap member in a first position on said external surface of said package member such that said first side is outwardly facing, and in a second position wherein said flap member is flipped over so that said second side is outwardly facing on said package member.

16. The package of personal care products as in claim 15, wherein said package member comprises at least one wall that is perpendicular to oppositely facing parallel walls, said end of said flap member hingedly attached to said perpendicular wall wherein in said first position, said flap member lies against a first wall of said package member, and in said second position said flap member lies against said oppositely facing parallel wall.

17. A package of personal care products, said package comprising:

an outer package member having said personal are products carried therein, said package member comprising an external surface having a desired nondescript aesthetic configuration that is generally not indicative of the personal care products within said package member;

a flap member having an end connected to said external surface of said package member, said flap member having a first side with product identifying indicia thereon, and a second opposite side having a surface with nondescript aesthetic indicia or designs that is generally not indicative of the personal care products within said package member;

attaching devices disposed to removably secure said flap member in a first position on said external surface of said package member such that said first side is outwardly facing, and in a second position wherein said flap member is flipped over so that said second side is outwardly facing on said package member; and wherein said aesthetic surface configuration of said flap second side generally matches that of said package member.

18. The package as in claim 15, wherein said attaching devices comprise hook-and-loop devices operatively configured between said first and second sides of said flap member and said external surface of said package member.

19. The package as in claim 15, wherein said attaching devices comprise a releasable adhesive operatively disposed between said first and second sides of said flap member and said external surface of said package member.

20. The package as in claim 15, wherein said end of said flap member is hingedly attached to said external surface of said package member.

21. The package as in claim 20 comprising a living hinge configured between said flap member and said external surface of said package member.

22. The package as in claim 15, further comprising necessary purchasing indicia provided on said external surface of said package member that is visible when said flap member is in said second position.

23. The package as in claim 15 wherein said flap member is also removable from said package member.

* * * * *